United States Patent
Lou et al.

(10) Patent No.: US 9,836,825 B2
(45) Date of Patent: Dec. 5, 2017

(54) DOSE MODULATED X-RAY SCANNING

(71) Applicant: SHENYANG NEUSOFT MEDICAL SYSTEMS CO., LTD., Shenyang (CN)

(72) Inventors: Shanshan Lou, Shenyang (CN); Ling Pang, Shenyang (CN)

(73) Assignee: SHENYANG NEUSOFT MEDICAL SYSTEMS CO., LTD., Shenyang (CN)

(*) Notice: Subject to any disclaimer, the term of this patent is extended or adjusted under 35 U.S.C. 154(b) by 170 days.

(21) Appl. No.: 14/843,754

(22) Filed: Sep. 2, 2015

(65) Prior Publication Data
US 2016/0063686 A1   Mar. 3, 2016

(30) Foreign Application Priority Data

Sep. 2, 2014  (CN) .......................... 2014 1 0445744

(51) Int. Cl.
*G06K 9/00* (2006.01)
*G06T 5/00* (2006.01)
*A61B 6/00* (2006.01)
*G06T 11/00* (2006.01)

(52) U.S. Cl.
CPC ............ *G06T 5/002* (2013.01); *A61B 6/5205* (2013.01); *A61B 6/5258* (2013.01); *A61B 6/542* (2013.01); *A61B 6/583* (2013.01); *G06T 11/005* (2013.01); *G06T 2207/10081* (2013.01); *G06T 2207/20192* (2013.01)

(58) Field of Classification Search
CPC .............................. G06T 11/005; G06T 5/002
See application file for complete search history.

(56) References Cited

U.S. PATENT DOCUMENTS

| 5,379,333 | A | * | 1/1995 | Toth | ........................ | A61B 6/032 378/108 |
| 5,400,378 | A | * | 3/1995 | Toth | ........................ | A61B 6/032 378/108 |

(Continued)

FOREIGN PATENT DOCUMENTS

| CN | 1615797 A | 5/2005 |
| CN | 103083032 A | 5/2013 |
| WO | 2013103790 A1 | 7/2013 |

OTHER PUBLICATIONS

State Intellectual Property Office of the People's Republic of China, Office Action Issued in Application No. 201410445744.4, dated May 31, 2017, 15 pages.

*Primary Examiner* — Gandhi Thirugnanam
(74) *Attorney, Agent, or Firm* — McCoy Russell LLP

(57) ABSTRACT

A method and a device for dose modulated X-ray scanning, where, according to an example of the method, a theoretical X-ray scanning dose for a scanning region may be calculated according to a target image quality standard set for the scanning region and a reference data level determined for the scanning region. Then, an X-ray attenuation difference between each data level corresponding to the scanning region and the reference data level may be calculated according to the theoretical X-ray scanning dose. In this way, a data level where the X-ray attenuation difference with the reference data level is higher than a threshold may be selected out from the data levels corresponding to the scanning region as a target to be de-noised, and a noise reduction may be performed for the target to be de-noised.

10 Claims, 3 Drawing Sheets

(56) References Cited

U.S. PATENT DOCUMENTS

| | | | | |
|---|---|---|---|---|
| 5,450,462 A * | 9/1995 | Toth | .................. | A61B 6/032 378/108 |
| 5,485,494 A * | 1/1996 | Williams | ............... | A61B 6/032 378/110 |
| 6,560,309 B1 * | 5/2003 | Becker | ................... | A61B 6/541 378/8 |
| 9,140,803 B2 * | 9/2015 | Bertram | ................ | A61B 6/032 |
| 9,351,700 B2 * | 5/2016 | Li | ......................... | A61B 6/542 |
| 2004/0101105 A1 * | 5/2004 | Segawa | ................ | A61B 6/032 378/108 |
| 2004/0247071 A1 * | 12/2004 | Dafni | .................... | A61B 6/032 378/16 |
| 2009/0141854 A1 * | 6/2009 | Hirokawa | .............. | A61B 6/032 378/4 |
| 2010/0303196 A1 * | 12/2010 | Zou | ....................... | A61B 6/032 378/5 |
| 2012/0114093 A1 * | 5/2012 | Yu | ......................... | A61B 6/032 378/8 |
| 2013/0202079 A1 * | 8/2013 | Yu | ....................... | A61B 6/5258 378/19 |
| 2013/0208971 A1 * | 8/2013 | Brown | .................... | G06T 5/001 382/131 |
| 2014/0105477 A1 * | 4/2014 | Ramirez Giraldo | ...... | G06T 5/50 382/131 |
| 2014/0270053 A1 * | 9/2014 | Larson | .................. | A61B 6/032 378/4 |
| 2015/0154766 A1 * | 6/2015 | Goshen | ................ | G06T 3/4053 382/131 |
| 2016/0063686 A1 * | 3/2016 | Lou | ......................... | G06T 5/002 382/131 |

* cited by examiner

DOSE MODULATED X-RAY SCANNING

CROSS-REFERENCE TO RELATED APPLICATIONS

The present application claims priority to Chinese Patent Application No. 201410445744.4, filed on Sep. 2, 2014, the entire contents of which are hereby incorporated by reference for all purposes.

BACKGROUND

Dose modulated X-ray scanning refers to the process of X-ray scanning in which the dose of the X-ray scanning varies synchronously with both attenuation difference of scanning position and angular difference of rotary scanning, so as to realize the noise uniformity of the X-ray scanning data from each of the scanning regions. During implementation of the dose modulated X-ray scanning, since the dose of the X-ray exposure is a fixed value in a same scanning region in a single exposure of bulb tube, the fact that the attenuation variance of the X-ray of the present scanning position in Z-direction scope could be relatively large will lead to significant differences among the noises of the X-ray scanning data of the present scanning position. For example, in a single exposure of bulb tube on the neck-shoulder junction, since the shoulder has an obviously larger area than the neck, then the fact that the attenuation variance of the X-ray of the neck-shoulder junction in Z-direction scope could be relatively large will lead to the scanning result of the shoulder with the larger area being blurred.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, MRI, Digital X-ray Machine, Ultrasound, PET (Positron Emission Tomography), Linear Accelerator, and Biochemistry Analyzer. Currently, NMS's products are exported to over 60 countries and regions around the globe, serving more than 5,000 renowned customers. NMS's latest successful developments, such as 128 Multislice CT scanner, Superconducting MRI, Linear Accelerator, and PET products, have led China to become a global high-end medical equipment producer. As an integrated supplier with extensive experiences in large medical equipment, NMS has been committed to the study of avoiding secondary potential harm caused by excessive X-ray irradiation to the subject (e.g., the patient) during the CT scanning process.

BRIEF DESCRIPTION OF DRAWINGS

Features of the present disclosure are illustrated by way of example and not limited in the following figures, in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Figure 1:
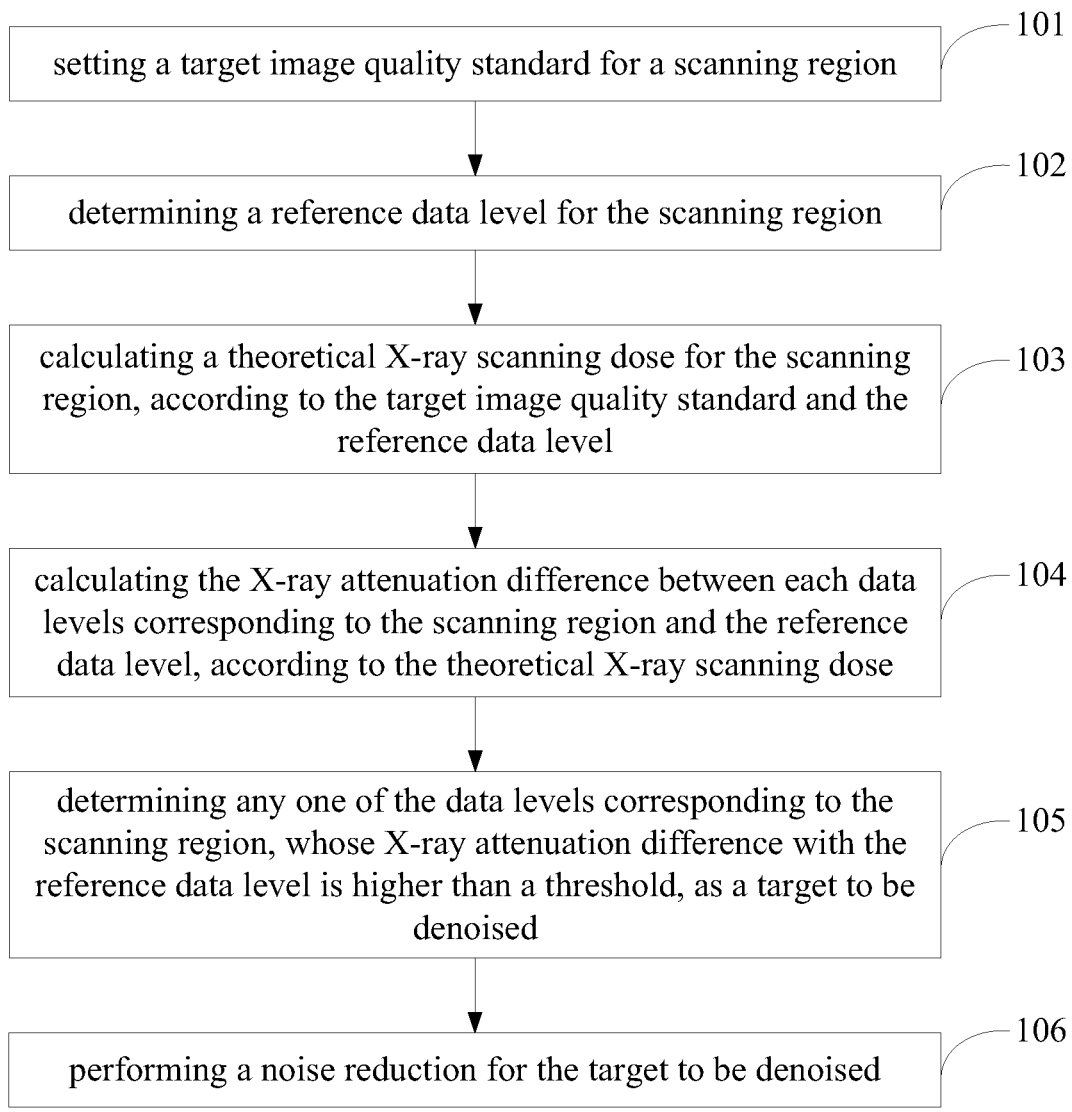
FIG. 1 illustrates a flow chart of a method for dose modulated X-ray scanning according to an example of the present disclosure.

Referring to FIG. 1, the present disclosure proposes a method for dose modulated X-ray scanning, which comprises:

In block 101, the method may include setting a target image quality standard for a scanning region. In an example, a target image quality standard for a scanning region can be set first, depending on the practical clinic scanning situation. Image quality standard may be image noise level, image SNR (Signal Noise Ratio), dose level, etc.

For example, assuming that image SNR may be used as an image quality standard, the parameter of the target image quality standard may be the ratio of the target image SNR to the standard image SNR of scanning protocol, and the range of the parameter may extend from 0.3 to 3.0. When the parameter of the target image quality standard is 1.0, the target image SNR equals the standard image SNR of the scanning protocol. Said standard image SNR of the scanning protocol refers to a default image SNR of the CT scanner. Similarly, when the parameter of the target image quality standard is 0.3 or 3.0, the target image SNR is the 0.3 or 3.0 times of the standard image SNR of the scanning protocol.

In block 102, the method may include determining a reference data level for the scanning region. In an example, the scanning region may correspond to multiple data levels, one of which may be taken as the reference data level so as to be the comparison standard for each of the multiple data levels afterwards.

In practical applications, the data level, which represents the average of the multiple data levels, may be taken as the reference data level. For example, the mean data level of the multiple data levels may be determined as the reference data level.

It should be understood that, blocks 101 and 102 may be implemented in different sequences according to the practical situation. There is no limitation in the present disclosure.

In block 103, the method may include calculating a theoretical X-ray scanning dose for the scanning region, according to the target image quality standard and the reference data level. In an example, the theoretical X-ray scanning dose is the necessary X-ray scanning dose on the scanning region to reach the target image quality standard in theory.

In practical implementation, first of all, a reference X-ray scanning dose for the reference data level is calculated according to the target image quality standard which was set previously. Secondly, the theoretical X-ray scanning dose for the scanning region is calculated according to the reference X-ray scanning dose and the number of the data levels corresponding to the scanning region. The theoretical X-ray scanning dose for the scanning region may be interpreted as the product of the reference X-ray scanning dose and the number of the data levels corresponding to the scanning region.

In an example, assuming that the total dose for a CT scanner to scan the scanning region is defined for a circle, the X-ray scanning dose is distributed according to the X-ray attenuation variance in each of the projection locations of the scanning. Here, the X-ray attenuation variance is the maximum X-ray attenuation in the projection locations of the scanning with respect to the reference data level. Generally, CT scanning may cover multiple layers of detectors. In this example, when calculating the theoretical X-ray scanning dose for the scanning region, it is common to choose data from one of the multiple layers of the detectors as the reference data level.

Specifically, the following formula may be applied to calculate the theoretical X-ray scanning dose for the scanning position:

$$N_{mod,i} = \frac{N_{0,All}}{\sum_{i=1}^{Np}\sqrt{A_{max,i}}} * \sqrt{A_{max,i}} \qquad \text{Formula 1}$$

$$N_{0,All} = Np * N_0 \qquad \text{Formula 2}$$

Wherein, $N_0$ is the X-ray emission intensity corresponding to the central channel of a CT scanner under a constant dose, and under a constant dose $N_0$ stays the same in each of the projection locations, then $N_p$ is the total number of projection locations of a scanning region for scanning a circle by a CT scanner. Further, $A_{max,i}$ is the maximum X-ray attenuation among each of the channels in the $i^{th}$ projection location, and $N_{mod,i}$ is the necessary X-ray scanning does for the $i^{th}$ projection location.

In block 104, the method may include calculating the X-ray attenuation differences between each data level corresponding to the scanning region and the reference data level according to the theoretical X-ray scanning dose.

In an example, after calculating a theoretical X-ray scanning dose for the scanning region, the X-ray attenuation of each data level corresponding to the scanning region is calculated, and the X-ray attenuation difference between each data level corresponding to the scanning region and the reference data level are determined according to the theoretical X-ray scanning dose.

In practical implementation, the X-ray attenuation diameter in an equivalent water phantom for each data level and the X-ray attenuation diameter in the equivalent water phantom for the reference data level are comparable. For example, first, the X-ray attenuation diameters in an equivalent water phantom for each data level corresponding to the scanning region are calculated according to the theoretical X-ray scanning dose. Second, the X-ray attenuation diameter differences in the equivalent water phantom between each data level corresponding to the scanning region and the reference data level are calculated.

For each data level corresponding to the scanning region, calculating the X-ray attenuation diameter in an equivalent water phantom comprises:

First, X-ray raw data of each data level corresponding to the scanning region is obtained, wherein, the raw data is obtained through N detector channels, i.e., through Formula 3;

$$\text{rawdata} = \{\mu_0 l_0, \mu_1 l_1, \ldots, \mu_p l_p\}, i = 0, 1, 2, 3, \ldots, N-1 \qquad \text{Formula 3}$$

Figure 2:
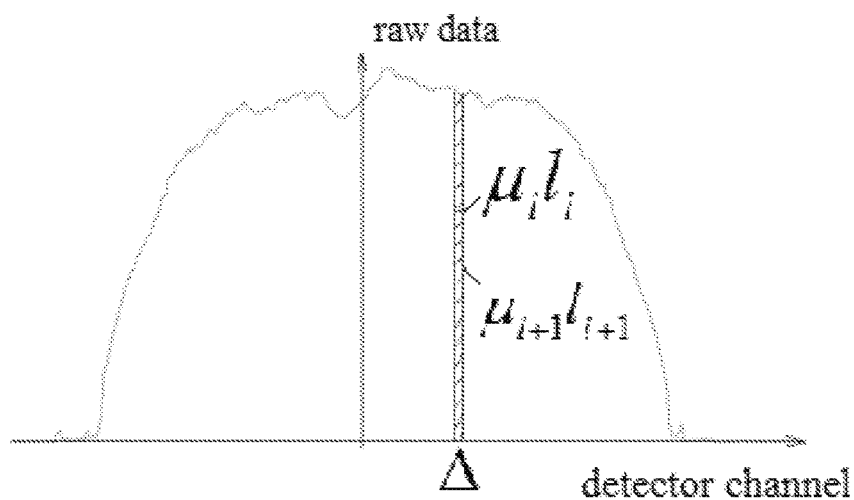
FIG. 2 illustrates an X-ray raw data coordinate schematic of any one of the data levels corresponding to a scanning region according to an example of the present disclosure.

Second, the total attenuation area of each data levels is calculated, based on the obtained X-ray raw data of each data level, with reference to FIG. 2, which illustrates an X-ray raw data coordinate schematic of any one of data levels in a scanning region.

Specifically, the total attenuation area of any data level can be calculated with the following formulas:

$$S = \sum_{i=0}^{N-1}(\mu_i l_i + \mu_{i+1}l_{i+1}) * \Delta/2 \qquad \text{Formula 4}$$

$$\Delta = R * \left(\frac{\alpha}{N}\right) \qquad \text{Formula 5}$$

Wherein, N is the number of channels, $\mu_i$ is the average X-ray attenuation factor of the subject on the $i^{th}$ channel, $l_i$ is the track of the subject on the $i^{th}$ channel, $\Delta$ is the distance between adjacent detectors, R is the rotation radius, and $\alpha$ is the sector angle of detector.

When calculating the total attenuation area S of any data level, the variance with height of a CT scanner bed should be considered. That is to say, the parameter $\Delta$ may be adjusted. If the scanning region is located in the center of the CT scanner, then it is not necessary to adjust the parameter $\Delta$. If the scanning region is dislocated from the center upwards, then the parameter $\Delta$ is adjusted smaller. If the scanning region is dislocated from the center downwards, then the parameter $\Delta$ is adjusted bigger. The parameter $\Delta$ can be adjusted based on the geometrical relationship of the CT scanner and the scanning region.

Lastly, the X-ray attenuation diameter $D_{scan}$ in an equivalent water phantom for the data level is calculated on the basis of the total attenuation area S of the data level through Formula 6:

$$D_{scan} = 2 * \text{sqrt}(\text{mean}(S)/(PI*\mu_{water})) \qquad \text{Formula 6}$$

Wherein, mean(s) is the mean value of the X-ray attenuation area of all the slices of the scanning region on Z-direction, $\mu_{water}$ is the X-ray attenuation factor in water.

In block 105, the method may including taking the data level, when X-ray attenuation difference compared with the reference data level is higher than a threshold, as a target to be de-noised (e.g., to remove or reduce noise).

In an example, a threshold may be set as the difference standard in advance. Specifically, the threshold may be set according to the scanning image quality requirements of the operator.

In practical implementation, after determining the X-ray attenuation differences between each data level and the reference data level, the data level whose difference is bigger than the pre-set threshold is determined as the target to be de-noised. For example, when the scanning region is the neck-shoulder junction, since the shoulder has an obviously larger area than the neck, then the attenuation variance of the X-ray of the neck-shoulder junction in Z-direction scope could be relatively large. In such a case, the difference between each data level of the neck-shoulder junction and the reference data level shall be larger than the pre-set threshold so that the data levels of the neck-shoulder junction shall be determined as the target to be de-noised.

In block 106, the method may include performing noise reduction on the target to be de-noised, so as to obtain a scanning image in accordance with the target image quality standard.

In practical applications, during the dose modulated X-ray scanning, the raw data of the target to be de-noised may be de-noised, and the de-noised X-ray raw data is saved, so as to finally obtain a scanning image in accordance with the target image quality standard utilizing the de-noised X-ray raw data.

For example, first, the X-ray raw data of the target to be de-noised is obtained. Second, a noise reduction is performed for the target to be de-noised according to the X-ray raw data so as to obtain a scanning image in accordance with the target image quality standard.

In this example, the noise reduction may also be based on the scanning image. For example, after determining the target to be de-noised, the X-ray raw data of the target to be de-noised can be marked on the head channel, and the original X-ray raw data without noise reduction is saved. In the consequent image reconstructing process, the image shall be de-noised according to the mark.

In practical applications, first, a primary scanning image may be obtained by scanning the scanning region with the theoretical X-ray scanning dose. And then, a noise reduction may be performed for the primary scanning image according to the target to be de-noised, so as to obtain a scanning image in accordance with the target image quality standard.

It shall be noticed that the noise reduction of this example can be conducted based on a combination of raw data and scanning images. There is no limitation in the specific de-noising method according the present disclosure.

In practical applications, the noise reduction based on raw data is a two sided filtering de-noising method, as shown below in Formula 7, Formula 8, and Formula 9:

$$\overline{Q}_1 = \frac{\sum_{j \in \omega_1} w_1(i, j) w_2(i, j) Q_j}{\sum_{j \in \omega_i} w_1(i, j) w_2(i, j)} \quad \text{Formula 7}$$

$$w_1(i, j) = \exp\left(-\frac{(i-j)^2}{2d^2}\right) \quad \text{Formula 8}$$

$$w_2(i, j) = \exp\left(-\frac{(Q_i - Q_j)^2}{2\sigma^2}\right) \quad \text{Formula 9}$$

Specifically, the X-ray raw data collected by the CT scanner is a two dimension data set by projection locations and channels, wherein i and j respectively represent locations of data points of the two dimension data, and $Q_i$ and $Q_j$ represent the values of the data points, $\hat{Q}_1$ is the convolution result data, and d and σ are regulatory factors. Looking at the formulas, $w_1$ is the Gaussian convolution with the distance to the center point as an independent variable, and $w_2$ is the Gaussian convolution with the difference from the center point as an independent variable, which can be considered as a confidence factor. The bigger the difference, the smaller the confidence factor, i.e., less contribution to de-noising.

Besides, the noise reduction based on scanning image may be a self-adaptive wiener filter de-noising method. The self-adaptive wiener filter adjusts the output of the filter according to a local variance of the scanning image, while the larger the local variance, the stronger the smoothing effect of the filter. The ultimate objective of such method is to minimize the mean square error e2=E{[f(x, y)−f^(x, y)]^2} between reconstructed image f^(x, y) and original image f(x, y). It shall be noticed that such method may be important for reserving edges and other high frequency portions of the scanning image.

In an example of the present disclosure, a scanning image in accordance with the target image quality standard is obtained by setting a target image quality standard for a scanning region, determining a reference data level for the scanning region, determining the target to be de-noised of the scanning region according to the target image quality standard and the reference data level, and performing a noise reduction for the target to be de-noised. Through determining the target to be de-noised and performing a noise reduction for the determined target, the present disclosure can improve the quality of the scanning image by a single exposure of bulb tube for dose modulated X-ray scanning.

Figure 3:
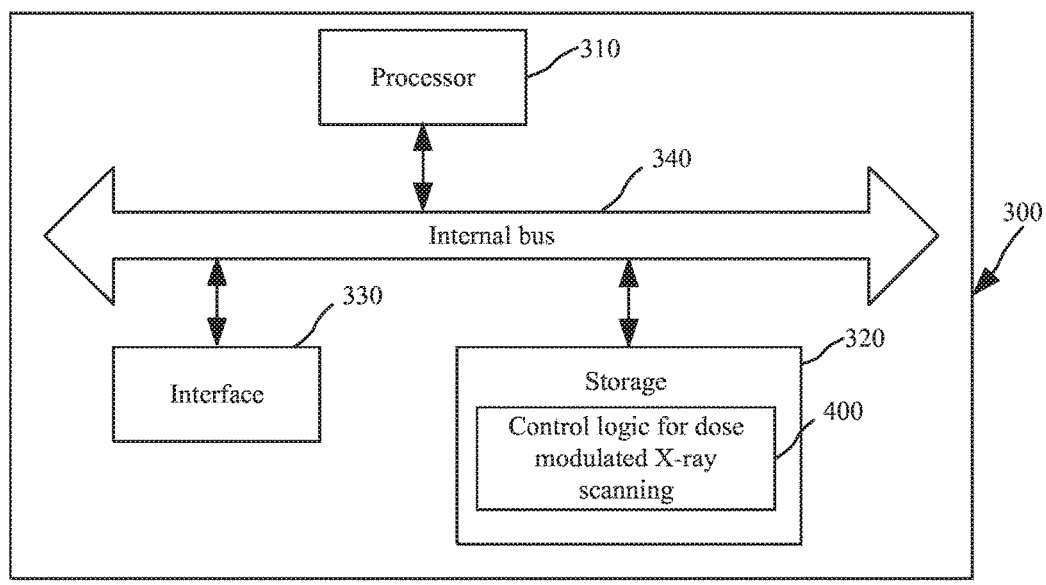
FIG. 3 illustrates a schematic diagram of hardware structure of a device for dose modulated X-ray scanning according to an example of the present disclosure.

FIG. 3 illustrates a hardware structural diagram of a device for dose modulated X-ray scanning according to an example of the present disclosure. The device 300 may comprise a processor 310 (such as Center Process Unit) and a machine readable storage medium 320, wherein, the processor 310 and the machine readable storage medium 320 are connected with each other through internal bus 340. In other available implementations, said device 300 may comprise an external interface 330 so as to communication with other devices or components.

In different examples, the machine readable storage medium 320 may be any electrical, magnetic, optical physical storage, or alike method. For example, the machine readable storage medium 320 can be RAM (Random Access Memory), volatile memory, non-volatile memory, flash disk, memory drive (for instance, hard disk drive), solid state drive, memory disc of any type (for instance, light disc or DVD), or any storage alike or combination thereof. The machine-readable storage medium 320 may include a non-transitory machine-readable medium storing instructions executable by processor 310 to perform one or more of the described methods/processes. For example, the processor 310, in combination with one or more other hardware devices (e.g., actuators, circuits, interfaces, etc.) may perform the methods/processes described herein.

Figure 4:
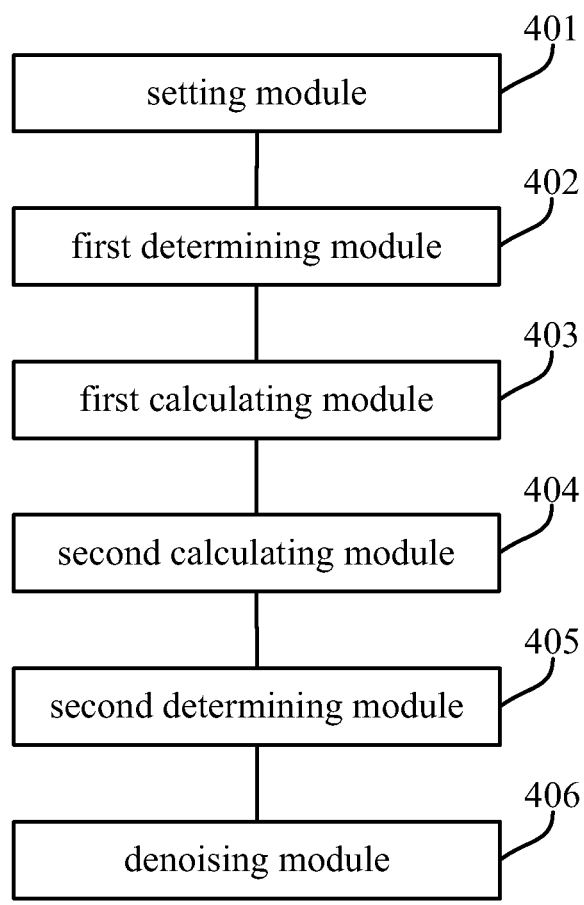
FIG. 4 illustrates a schematic diagram of function modules of control logic for dose modulated X-ray scanning according to an example of the present disclosure.

Furthermore, the machine readable storage medium 320 stores a control logic 400 for dose modulated X-ray scanning. FIG. 4 illustrates a schematic diagram of function modules of control logic for dose modulated X-ray scanning in one example. Functionally, the control logic 400 for the dose modulated X-ray scanning, comprises:

a setting module 401 for setting a target image quality standard for a scanning region;

a first determining module 402 for determining a reference data level for the scanning region;

a first calculating module 403 for calculating a theoretical X-ray scanning dose for the scanning region according to the target image quality standard and the reference data level;

a second calculating module 404 for calculating the X-ray attenuation difference between each data level corresponding to the scanning region and the reference data level according to the theoretical X-ray scanning dose;

a second determining module 405 for determining any one of the data levels corresponding to the scanning region, which X-ray attenuation difference with respect to the reference data level is higher than a threshold as a target to be de-noised; and a de-noising module 406 for performing a noise reduction for the target to be de-noised so as to obtain a scanning image in accordance with the target image quality standard.

Wherein, the first calculating module 403 may comprise:

a first calculating sub-module, for calculating a reference X-ray scanning dose for the reference data level according to the target image quality standard; and a second calculating sub-module, for calculating the theoretical X-ray scanning dose for the scanning region according to the reference X-ray scanning dose and the number of data levels corresponding to the scanning region.

Wherein, the second calculating module 404 may comprise:

a third calculating sub-module for calculating the X-ray attenuation diameter in an equivalent water phantom for each data level corresponding to the scanning region according to the theoretical X-ray scanning dose; and a fourth calculating sub-module, for calculating the X-ray attenuation diameter difference in the equivalent water phantom between each data level corresponding to the scanning region and the reference data level.

In an example, the de-noising module 406 may comprise:

an obtaining module for obtaining the X-ray raw data of the target to be de-noised; and a de-noising sub-module for performing a noise reduction for the target to be de-noised, according to the X-ray raw data, so as to obtain a scanning image in accordance with the target image quality standard.

In another example, the de-noising module 406 may comprise:

a scanning sub-module for obtaining a primary scanning image by scanning the scanning region with the theoretical X-ray scanning dose; and a second de-noising sub-module for performing a noise reduction for the primary scanning image, according to the target to be de-noised, so as to obtain a scanning image in accordance with the target image quality standard.

The following example may be implemented in software which is described in the execution of the control logic 400 for dose modulated X-ray scanning by the device 300. In such example, the control logic 400 shall be considered as computer instructions stored in the machine readable storage medium 320. When the processor 310 on the device 300 implements the control logic 400, the processor 310, by reading the instructions of corresponding functional modules in the control logic 400 for dose modulated X-ray scanning in the machine readable storage medium 320, implements:

setting a target image quality standard for a scanning region;

determining a reference data level for the scanning region;

calculating a theoretical X-ray scanning dose for the scanning region according to the target image quality standard and the reference data level;

calculating the X-ray attenuation difference between each data level corresponding to the scanning region and the reference data level, according to the theoretical X-ray scanning dose;

determining the data level corresponding to the scanning region, which X-ray attenuation difference with the reference data level is higher than a threshold, as a target to be de-noised; and performing a noise reduction for the target to be de-noised.

Furthermore, the processor 310, by reading the instructions of corresponding functional modules in the control logic 400 for dose modulated X-ray scanning in the storage medium 320, implements:

calculating a reference X-ray scanning dose for the reference data level, according to the target image quality standard; and calculating the theoretical X-ray scanning dose for the scanning region, according to the reference X-ray scanning dose and the number of the data levels corresponding to the scanning region.

Furthermore, the processor 310, by reading the instructions of corresponding functional modules in the control logic 400 for dose modulated X-ray scanning in the storage medium 320, implements:

calculating the X-ray attenuation diameter in an equivalent water phantom for each data level corresponding to the scanning region, according to the theoretical X-ray scanning dose; and calculating the X-ray attenuation diameter difference in the equivalent water phantom between each data level corresponding to the scanning region and the reference data level.

Furthermore, the processor 310, by reading the instructions of corresponding functional modules in the control logic 400 for dose modulated X-ray scanning in the storage medium 320, implements:

obtaining the X-ray raw data of the target to be de-noised; and performing a noise reduction for the target to be de-noised, according to the X-ray raw data, so as to obtain a scanning image in accordance with the target image quality standard.

Furthermore, the processor 310, by reading the instructions of corresponding functional modules in the control logic 400 for dose modulated X-ray scanning in the storage medium 320, implements:

obtaining a primary scanning image by scanning the scanning region with the theoretical X-ray scanning dose; and performing a noise reduction for the primary scanning image, according to the target to be de-noised, so as to obtain a scanning image in accordance with the target image quality standard.

The foregoing disclosure is merely illustrative of some examples of the present disclosure but not intended to limit the present disclosure, and any modifications, equivalent substitutions, adaptations, thereof made without departing from the spirit and scope of the disclosure shall be encompassed in the claimed scope of the present disclosure.

The methods, processes and units described herein may be implemented by hardware (including hardware logic circuitry), software or firmware, or a combination thereof. The term "processor" is to be interpreted broadly to include a processing unit, ASIC, logic unit, programmable gate array, etc. The processes, methods, and functional units may all be performed by one or more of the processors. Reference in this disclosure or the claims to a "processor" should thus be interpreted to mean "one or more processors".

Further, the processes, methods, and functional units described in this disclosure may be implemented in the form of a computer software product. The computer software product is stored in a storage medium and comprises a plurality of instructions for making a processor to implement the methods recited in the examples of the present disclosure.

The figures are some illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described examples, without departing from the broad general scope of the present disclosure. The present disclosure is, therefore, to be considered in all respects as illustrative and not restrictive.

The invention claimed is:

1. A method for dose modulated X-ray scanning, the method comprising:
   setting a target image quality standard for a scanning region;
   determining a reference data level for the scanning region;
   calculating a theoretical X-ray scanning dose for the scanning region, according to the target image quality standard and the reference data level;
   calculating an X-ray attenuation difference between each data level corresponding to the scanning region and the reference data level, according to the theoretical X-ray scanning dose;
   identifying any one of the data levels corresponding to the scanning region, whose X-ray attenuation difference with the reference data level is higher than a threshold, as a target to be de-noised; and
   performing a noise reduction for the target to be de-noised.

2. The method according to claim 1, wherein said calculating a theoretical X-ray scanning dose for the scanning region comprises:
   calculating a reference X-ray scanning dose for the reference data level, according to the target image quality standard; and
   calculating the theoretical X-ray scanning dose for the scanning region, according to a reference X-ray scanning dose and a number of the data levels corresponding to the scanning region.

3. The method according to claim 1, wherein said calculating the X-ray attenuation differences between each data level corresponding to the scanning region and the reference data level comprises:
   calculating X-ray attenuation diameters in an equivalent water phantom for each data level corresponding to the scanning region according to the theoretical X-ray scanning dose; and
   calculating X-ray attenuation diameter differences in the equivalent water phantom between each data level corresponding to the scanning region and the reference data level.

4. The method according to claim 1, wherein said performing a noise reduction for the target to be de-noised comprises:
   obtaining X-ray raw data of the target to be de-noised; and
   performing a noise reduction for the target to be de-noised, according to the X-ray raw data, so as to obtain a scanning image in accordance with the target image quality standard.

5. The method according to claim 1, wherein said performing a noise reduction for the target to be de-noised, comprises:
   obtaining a primary scanning image by scanning the scanning region with the theoretical X-ray scanning dose; and
   performing a noise reduction for the primary scanning image, according to the target to be de-noised, so as to obtain a scanning image in accordance with the target image quality standard.

6. A device for dose modulated X-ray scanning, the device comprising:
   a processor which reads instructions corresponding to a control logic for dose modulated X-ray scanning in a storage medium and executes the instructions to:
   set a target image quality standard for a scanning region;
   determine a reference data level for the scanning region;
   calculate a theoretical X-ray scanning dose for the scanning region, according to the target image quality standard and the reference data level;
   calculate an X-ray attenuation difference between each data level corresponding to the scanning region and the reference data level, according to the theoretical X-ray scanning dose;
   identify any one of the data levels corresponding to the scanning region, whose X-ray attenuation difference with the reference data level is higher than a threshold, as a target to be de-noised; and
   perform a noise reduction for the target to be de-noised.

7. The device according to claim 6, wherein the instructions further cause the processor to:
   calculate a reference X-ray scanning dose for the reference data level, according to the target image quality standard; and
   calculate the theoretical X-ray scanning dose for the scanning region, according to the reference X-ray scanning dose and a number of the data levels corresponding to the scanning region.

8. The device according to claim 6, wherein the instructions further cause the processor to:
   calculate an X-ray attenuation diameter in an equivalent water phantom for each data level corresponding to the scanning region, according to the theoretical X-ray scanning dose; and
   calculate an X-ray attenuation diameter difference in the equivalent water phantom between each data level corresponding to the scanning region and the reference data level.

9. The device according to claim 6, wherein the instructions further cause the processor to:
   obtain X-ray raw data of the target to be de-noised; and
   perform a noise reduction for the target to be de-noised, according to the X-ray raw data, so as to obtain a scanning image in accordance with the target image quality standard.

10. The device according to claim 6, wherein the instructions further cause the processor to:
    obtain a primary scanning image by scanning the scanning region with the theoretical X-ray scanning dose; and
    perform a noise reduction for the primary scanning image, according to the target to be de-noised, so as to obtain a scanning image in accordance with the target image quality standard.

* * * * *